(12) United States Patent
Bartelmez et al.

(10) Patent No.: US 6,869,795 B1
(45) Date of Patent: Mar. 22, 2005

(54) ANTISENSE COMPOSITIONS AND CANCER-TREATMENT METHODS

(75) Inventors: Stephen H. Bartelmez, Seattle, WA (US); Patrick L. Iversen, Corvallis, OR (US)

(73) Assignee: AVI BioPharma, Inc., Corvallis, OR (US)

(*) Notice: Subject to any disclaimer, the term of this patent is extended or adjusted under 35 U.S.C. 154(b) by 0 days.

(21) Appl. No.: 09/684,061

(22) Filed: Oct. 6, 2000

Related U.S. Application Data (60) Provisional application No. 60/158,340, filed on Oct. 7, 1999.

(51) Int. Cl.[7] .......................... C12N 5/00; C12N 15/63; C12Q 1/68; C12P 19/34; C07H 21/02
(52) U.S. Cl. .......................... 435/375; 435/6; 435/91.1; 435/455; 536/23.1; 536/24.31; 536/24.5
(58) Field of Search .................. 435/6, 91.1, 91.31, 435/375, 455; 514/44; 536/23.1, 24.31, 24.5, 25.4

(56) References Cited

FOREIGN PATENT DOCUMENTS

WO    WO 93/21202    10/1993

OTHER PUBLICATIONS

Srour, E.F. et al. J. of Hematotherapy, vol. 8: 93–102 (1999).*
Engel, B.C. et al. Frontiers in Bioscience, vol. 4: e26–33, May, 1999.*
Karen Pihl-Carey, Isis To Restructure As Crohn's Disease Drug Fails In Phase III, The Daily Biotechnology, vol. 10, No. 239, pp. 1–2.*
Andrea D. Branch, A good antisense molecule is hard to find, TIBS 23—Feb. 1998, pp. 45–50.*
Mitani K et al., Oncogenic potentials of the AML–1/EVI–1 fusion protein derived from the t (3; 21) (q26; q22) translocation in blastic crisis of chronic myelocytic leukemia, Journal Article.*
Giorgio Palu' et al., In pursuit of new developments for gene therapy of human diseases, Journal of Biotechnology 68 (1999) pp. 1–13.*
Stanley T. Crooke, Antisense Research and Application, pp. 1–50.*
Hendrikx, P.J., et al., Blood, 94: 682, (1999).
Mitani, K., et al., British Journal of Haematology, 90: 711–714, (1995).
Privitera, E., et al., Leukemia, 11: 2045–2048, (1997).
Shelly, L., et al., Journal of Cellular Biochemistry, 73: 164–175, (1999).
Summerton, J., et al., Antisense and Nucleic Acid Drug Development, 7: 187–195, (1997).
Tsai, S., et al., Bood, 96: 950–957, (2000).
Yagi, M., et al., Proc. Natl. Acsd. Sci. USA, 96: 8126–81, (1999).
International Search Report PCT/US 00/27636.
Ardhammar, M., et al., "In Vitro Membrane Penetration of Modified Peptide Nucleic Acid (PNA)" *Journal of Biomolecular Structure & Dynamics* 17(1):33–40 (1999).
Autuori, F., et al., "'Tissue' Transglutaminase and Apoptosis" *Advances in Biochemical Engineering/Biotechnology* 62: 129–136 (1998).
Brooks, D.J., et al., "Expression of the zinc finger gene EVI–1 in ovarian and other cancers" *British Journal of Cancer* 74:1518–1525 (1996).
Gray, G.E., et al., "Human Ligands of the Notch Receptor" *American Journal of Pathology* 154(3):785–794 (1999).
Gustincich, S., et al., "The Human *Serum Deprivation Response* Gene (*SDPR*) Maps to 2q32–q33 and Codes for a Phosphatidylserine–Binding Protein" *Genomics* 57:120–129 (1999).
Hayward, C.P.M., et al., "Multimerin Processing by Cells With and Without Pathways for Regulated Protein Secretion" *Blood* 94(4):1337–1347 (1999).
Larsen, H.J., et al., "Antisense properties of peptide nucleic acid" *Biochimica et Biophysica Acta* 1489 pp. 159–166 (1999).
Sabo, S.L., et al., "Regulation of β–Amyloid Secretion by FE65, an Amyloid Protein Precursor–binding Protein" *The Journal of Biological Shemistry* 274(12):7952–7957 (1999).

* cited by examiner

*Primary Examiner*—John L. LeGuyader
*Assistant Examiner*—Jane Zara
(74) *Attorney, Agent, or Firm*—Linda R. Judge; Jacqueline F. Mahoney; Lee Ann Gorthey (57) ABSTRACT

A composition antisense oligomer directed to an mRNA preferentially expressed together with methods for treating stem cells with such a composition to increase the number of lineage committed progenitor cells and their progeny, and/or slow the growth of cancer cells. Also described is the use of such compositions and antisense oligonucleotide-treated stem cells in methods for treatment of cancer.

5 Claims, 3 Drawing Sheets

ANTISENSE COMPOSITIONS AND CANCER-TREATMENT METHODS

This application claims priority of U.S. Provisional Application No. 60/158,340 filed Oct. 7, 1999, which is incorporated in its entirety herein by reference.

FIELD OF THE INVENTION

The present invention relates to antisense oligonucleotide compositions for promoting the differentiation of hematopoietic stem cells and methods for the treatment of hematopoietic stem cells with such compositions in a manner effective to retard or arrest the growth of cancer.

REFERENCES

Abbas, A K, et al., Eds., *Cellular and Molecular Immunology*, 3rd edition, W B Saunders Co., 394–405, (1997).
Agrawal, S., et al., *Proc. Natl. Acad. Sci. USA* 87(4):1401–5, (1990).
Akhtar, S., et al., *Nuc. Res.* 19:5551–5559, (1991).
Anderson, C. M., et al., *J. veurochem* 73(2):867–873, (1999).
Anderson, K. P., et al., *Antimicrob. Agents and Chemotherapy* 40(9):2004–2011, (1996).
Autuori, F., et at, *Adv Biochem Eng Biotechnol* 62:129–36, (1998).
Baker, C., et al., *Nuc. Ac. Res.* 18:3537, (1990).
Bennett, M. R., et al., *Circulation* 92(7):1981–1993, (1995).
Bertoncello I et al., *Exp Hematol* 19(2):95–100, (1991).
Blake, et al., *Biochem.* 24:6139, (1985).
Bonham, M. A., et al., *Nucleic Acids Res.* 23(7):1197–1203, (1995).
Boudvillain, M., et al., *Biochemistry* 36(10):2925–31, 1997).
Brooks, D. J., et al., *Br J Cancer* 74(10):1518–25, (1996).
Calabrett, et al., *Proc. Natl. Acad. Sci. USA* 88:2351, (1991).
Cohen, et al., *Antisense Res. & Dev.* 2:191, (1991).
Fichelson, S., et al. *Leukemia* 6:93, (1992).
Gee, J. E., et al., *Antisense & Nucleic Acid Drug Dev.* 8:103–111, (1998).
Giles, R. V., et al., *Anticancer Drug Des.* 8(1):33–51, (1993).
Gray, G. E., et al., *Am J. Pathol* 154(3):785–94, (1999).
Gregoriadis, G., Chapter 14, *Liposomes, Drug Carriers in Biology and Medicine*, pp. 287–341, Academic Press, (1979).
Gustincich, S., et al., *Genomics* 57(1):120–9, (1999).
Hayward, C. P., and Kelton, J. G., *Curr Opin Hematol* 2(5):33944, (1995).
Hayward, C. P., *Clin Invest Med* 20(3):176–87, (1997).
Hudziak, R. M., et al, *Antisense and Nucleic Acid Drug Dev.* 6(4):267–272, (1996).
Lappalainen, et al., *Antiviral Res.* 23, 119, (1994).
Loke, S. L., et al., *Proc. Nat. Acad. Sci. USA* 86:3474, (1989).
Luo, B., et al., *Mol Cell Biol L*7(10):6057–67, (1997).
McManaway, et al., *Lancet* 335:808, (1990).
McNiece, I. K., *Int J Cell Cloning* 8(3):146–60, (1990).
Milner L A et al., *Blood,* 83(8) 2057–62, (1994).
Milner L A and Bigas A, *Blood* 93(8):2431–48, (1999).
Moffat, *Science* 253:510, (1991).
Morishita, K., et al., *Cell* 54:831, (1998).
Nagata K, et al., *J Biol Chem* 264:17000–17005 (1989).
Nielsen, P. E., *Annu Rev Biophys Biomol Struct.* 24:167–83, (1995).
Nunes I, et al., *J Cell Biol* 136:1151–1163, (1997).
Ogawa, S., et al., *Hum Cell* 2(4):323–32, (1996).
Ohyashiki, K., et al., *Leukemia* 8(12):2169–73, (1994).
Ogawa, M., et al., *Science* 273:242–245, (1996).
Pari, G. S., et al., *Antimicrob. Agents and Chemotherapy* 39(5):1157–1161 (1995).
Reed, et al., *Cancer Res.* 50:6565, (1990).
Russo, T., et al., *FEBS Lett* 34(1–2): 1–7, (1998).
Sabo, S. L., et al., *J Biol Chem* 19:274(12):7952–7, (1999).
Sambrook, J., et al., MOLECULAR CLONING: A LABORATORY MANUAL. Cold Spring Harbor, N.Y., Cold Spring Harbor Laboratory, (1989).
Schmidt-Wolf, I. G., et al., *J Exp Med* 174(1): 139–49, (1991).
Seabra, M. C., et al., *J Biol Chem* 270(41):24420–7, (1995).
Smith, L. G., et al., *Proc. Nat. Acad. Sci. USA,* 88:2788–2792 (1991).
Spitzer, F. and Eckstein, F., *Nuc. Ac. Res.* 16: 11691–11704, (1988).
Summerton, J., et al., *Antisense Nucleic Acid Drug Dev* 7(2):63–70, (1997).
Szczylik, et al, *Science* 253:562, (1991).
Tanaka, I., et al., *Int J Hematol* 69(2):70–4, (1999).
Tidd, et al., *Anti-Cancer Drug Design* 3:117, (1988).
Toulme, J. J., et al., *Biochimie* 78(7):663–73, (1996).
Toyama, H., et al., *Jpn J Cancer Res* 87(3):269–74, (1996).
Uhlmann, et al., *Chemical Reviews* 90: 543–584, (1990).
Uhlmann, et al., *Antisense Oligonucleotides: A New Therapeutic Principles, Chemical Reviews*, Volume 90, No. 4, pages 544–584, June (1990).
Watson, et al., *Cancer Res.* 51:3996, (1991).
Wilson, J. D., et al., HARRISON'S PRINCIPLES OF INTERNAL MEDICINE, 12th Ed., McGraw-Hill, Inc., New York, pp 268–269 and 285–288 (1991).
Wolf, N. S., et al., *Exp Hematol* 21(5):614–22, (1993).
Wu GY and Wu CH, *J. Biol. Chem.* 262:44294432, (1987).
Yakubov, L. A., et al., *Proc. Nail. Acad. Sci. USA* 86:6454, (1989).

BACKGROUND OF THE INVENTION

The hematopoietic stem cell (HSC) is a pluripotent progenitor cell that has been characterized as a cell that is transplantable, can self-replicate and has multilineage potential. Differentiation of HSCs results in a loss of such multilineage potential, and corresponding lineage commitment. It has been demonstrated that self-renewal of HSC occurs in vivo, as indicated by transplantation studies wherein a single HSC repopulated the marrow of an immunodeficient mouse (Smith, et al., 1991; Osawa, et al., 1996). It has also been demonstrated that hematopoietic stem cells can be infected with recombinant retroviruses, and can serve as cellular targets for gene therapy (Keller and Snodgrass, 1990). (See also, Schmidt-Wolf, I. G., et al., 1991.)

Patients suffering from various cell-based diseases including, but not limited to, myeloproliferative diseases, blood cell proliferative diseases and autoimmune diseases often have an imbalance in the number of cells of particular lineages. In addition, patients undergoing chemotherapy or irradiation often have defective hematopoiesis.

It follows that the modulation of hematopoietic cell processes in patients suffering from any of the above pathological conditions has numerous clinical utilities and that such cells are targets for genetic engineering-based therapies (Wilson, J. D., et al, 1991).

Inhibition of the expression of genes associated with cellular development has been used to modify developmental processes toward directions which are not dependent on the expression of the inhibited gene or genes. Inhibition of genes associated with cellular development has been achieved using antisense technology.

It has been demonstrated that antisense oligonucleotides can be designed to specifically interfere with synthesis of a target protein of interest (Moffat, 1991). Antisense oligonucleotides of 15–20 bases are usually long enough to have one complementary sequence in the mammalian genome. In addition, they hybridize well with their target mRNA (Cohen, et al., 1991).

Due to their hydrophobicity, antisense oligonucleotides interact well with phospholipid membranes (Akhtar, S., et al., 1991), and it has been suggested that following the interaction with the cellular plasma membrane, oligonucleotides are actively transported into living cells (Loke, S. L., et al., 1989; Yakubov, L. A., et al., 1989; Anderson, C. M., et al., 1999).

Inhibition of genes associated with cellular development has been achieved using antisense technology, however, naturally occurring oligonucleotides have a nuclease-sensitive phosphodiester backbone.

Such naturally occurring oligonucleotides may be modified to render them resistant to degradation by nucleases, e.g., by utilizing a methylphosphonate, phosphorothioate or phosphoamidate linkage instead of a phosphodiester one (Spitzer and Eckstein, 1988; Baker, et al, 1990; Hudziak, 1996).

Nonionic methyl-phosphonate analogs were predicted to exhibit increased cellular uptake (Blake, et al., 1985), however, antisense methylphosphonate oligomers were shown to be incapable of inhibiting N-ras expression in vitro (Tidd, et al., 1988), whereas the in vitro translation of several oncogene mRNAs was successfully blocked by phosphodiester and/or phosphorothioate antisense oligonucleotides. See, for example, McManaway, et al., 1990, and Watson, et al., 1991 (c-myc inhibition); Reed, et al., 1990 (bcl-2 inhibition); Calabrett, et al., 1991 (myb inhibition); Szczylik, et al., 1991 (bcr-abl inhibition).

Morpholino oligonucleolides have been demonstrated to exhibit high binding affinity for RNA targets, and the uncharged backbone favors uptake into cells and reduces non-specific binding interactions. (See, e.g., Summerton, et al., 1997).

For therapeutic purposes, it would be desirable to provide a means to modulate hematopoietic stem cell differentiation using an agent which acts specifically on hematopoietic stem cells.

SUMMARY OF THE INVENTION

The invention provides methods and compositions for promoting the differentiation of stem cells. In a preferred aspect, the invention provides a composition comprising an antisense oligomer directed to a sequence spanning the mRNA translational start codon of a gene preferentially expressed in stem cells.

An antisense oligomer of the invention is typically characterized by one or more of: (I) a length of about 12 to 25 bases; (2) a backbone which is substantially uncharged; (3) the ability to hybridize with the complementary sequence of a target RNA with high affinity at a Tm greater than 50° C.; (4) nuclease resistance; (5) the capability for active or facilitated transport into cells; and (6) a structure selected from the group consisting of the structures presented in FIGS. 2A-A through 2E-E.

In another preferred aspect, the antisense oligomer has a sequence selected from the group presented as SEQ ID NO:1, SEQ ID NO:2, SEQ ID NO:3, SEQ ID NO:4, SEQ ID NO:5, SEQ ID NO:6, and SEQ ID NO:7, SEQ ID NO:10, SEQ ID NO:11 and SEQ ID NO:12, where the compound is targeted against an mRNA transcribed by the EVI-1 zinc finger gene, the serum deprivation response (SDR) gene, the multimerin gene, the tissue transglutaminase gene, the Fe65 gene, the RAB27 gene, the human Jagged2 gene, the human Notch1 (Tan-1) gene, the human Notch2 gene, the human Notch3 gene and the murine Notch1 gene, respectively.

In one preferred embodiment, the antisense oligomer has the sequence presented as SEQ ID NO:1.

In a further aspect, the invention provides methods for treating a human cancer patient, by either (A) direct administration of a composition comprising one or more antisense oligomers directed to an mRNA preferentially expressed in stem cells; and/or (B) obtaining a stem cell-containing cell population from a subject, treating the cell population in manner effective to enrich the cell population for stem cells; and exposing the enriched stem cell population, ex vivo, to one or more of such antisense oligomers, followed by infusing the antisense oligomer-treated cell population into the human cancer patient. In practicing the invention, either process is carried out in a manner effective to (i) increase the number of lineage committed progenitor cells and their progeny in the peripheral circulation of the subject, and/or (ii) effect a slowing or diminution of the growth of cancer cells or a solid tumor, or a reduction in the total number of cancer cells or total tumor burden.

Such treatment methods may be carried out alone or in combination with further treatment by radiation or chemotherapy.

In one application of the method, the stem cells are pluripotent hematopoietic stem cells and the treatment of the HSC with an antisense oligomer composition of the invention promotes the transition of such HSC from a quiescent state, resulting in an increase in the number of more differentiated cells, such as monocytes, granulocytes, platelets, lymphocytes and red blood cells, and preferably an increase in neutrophils and/or platelets.

These and other objects and features of the invention will become more fully apparent when the following detailed description is read in conjunction with the accompanying figures and examples.

BRIEF DESCRIPTION OF THE FIGURES

FIGS. 2A-A through 2E-E show the repeating subunit segment of exemplary morpholino oligonucleotides, constructed using subunits A–E, respectively, of FIG. 1.

DETAILED DESCRIPTION OF THE INVENTION

1. Definitions

The terms below, as used herein, have the following meanings, unless indicated otherwise:

As used herein, the term "a cell population enriched for hematopoietic stem cells" refers to the cell population obtained using the positive and negative selection techniques described herein, wherein the hematopoietic stem cells may be LTR- or STR-HSCs.

As used herein, the terms "long term repopulating hematopoietic stem cells" and "LTR-HSC", refer to hematopoietic stem cells that are transplantable, and upon differentiation contribute to all lineages of hematopoietic cells for an undefined period of time when transplanted into totally immunosuppressed recipients. LTR-HSC do not undergo clonal extinction.

As used herein, the term "short term repopulating hematopoietic stem cells" or "STR-HSC", refers to murine hematopoietic stem cells that are transplantable, and contribute to all lineages of hematopoietic cells for a period of from about one week to 6 months, then undergo clonal extinction when transplanted into immunosuppressed recipients.

The term "clonal extinction", as used herein refers to the terminal differentiation of a single hematopoietic stem cell and all the progeny produced by clonal expansion of that cell, such that no more daughter cells are produced from the initial clone.

The term "pluripotent hematopoietic stem cells" refers to hematopoietic stem cells, capable of differentiating into all the possible cell lineages.

As used herein, the term "high proliferative potential colony forming cells" or "HPP-CFCs", as used herein relative to hematopoietic stem cells refers to murine cells that proliferate in response to rat rSCF, mouse rIL-3 and human rIL-6. The cells proliferate in semi-solid media, such as agar or methyl cellulose or as single cells in liquid culture, and form macroclones which have a diameter greater than 1 mm, generally having greater than 100,000 cells per clone with dense multicentric centers. This population includes all murine HSCs, however, not all HPP-CFC are HSCs, and the HPP-CFC assay is not a specific assay for LTR-HSC. In contrast, low proliferative potential (LPP) clones contain from 2 to 100,000 cells per clone.

As used herein, "lineage-committed hematopoietic stem cells" are hematopoietic stem cells that have differentiated sufficiently to be committed to one or more particular cell lineages, but not all cell lineages.

As used herein, the term "lin–" or "lineage-depleted", refers to a cell population which lacks expression of cell surface antigens specific to T-cells, B-cells, neutrophils, monocytes and erythroid cells, and does not express antigens recognized by the "YW 25.12.7" antibody. (See, e.g., Bertoncello I et al., 1991.)

As used herein, the terms "develop", "differentiate" and "mature" are used interchangeably and refer to the progression of a cell from a stage of having the potential to differentiate into multiple cellular lineages to becoming a more specialized cell committed to one or more defined lineages.

As used herein, the term "purified", relative to hematopoietic stem cells refers to HSCs that have been enriched (isolated or purified) relative to some or all of the other types of cells with which they are normally found in a particular tissue in nature, e.g., bone marrow or peripheral blood. In general, a "purified" population of HSCs has been subjected to density gradient fractionation, lineage depletion and positive selection for c-kit and Sca-1 expression in addition to low level staining with both Hoechst 33342 and Rhodamine 123.

As used herein, the terms "antisense oligonucleotide" and "antisense oligomer" are used interchangeably and refer to a sequence of nucleotide bases and a subunit-to-subunit backbone that allows the antisense oligomer to hybridize to a target sequence in an RNA by Watson-Crick base pairing, to form an RNA:oligomer heteroduplex within the target sequence, typically with an mRNA. The oligomer may have exact sequence complementarity to the target sequence or near complementarity. Such antisense oligomers may block or inhibit translation of the mRNA containing the target sequence; and/or (1) modify the processing of an mRNA to produce a splice variant of the mRNA. An antisense oligomer may inhibit gene transcription, bind to double-stranded or single stranded sequences and may be said to be "directed to" a sequence with which it hybridizes."

Exemplary structures for antisense oligonucleotides for use in the invention include the β-morpholino subunit types shown in FIG. 1A-E. It will be appreciated that a polymer may contain more than one linkage type.

Subunit A in FIG. 1 contains a 1-atom phosphorous-containing linkage which forms the five atom repeating-unit backbone shown at A—A in FIG. 2, where the morpholino rings are linked by a 1-atom phosphonamide linkage.

Subunit B in FIG. 1 is designed for 6-atom repeating-unit backbones, as shown at B—B, in FIG. 2. In structure B, the atom Y linking the 5' morpholino carbon to the phosphorous group may be sulfur, nitrogen, carbon or, preferably, oxygen. The X moiety pendant from the phosphorous may be any of the following: fluorine; an alkyl or substituted alkyl; an alkoxy or substituted alkoxy; a thioalkoxy or substituted thioalkoxy; or, an unsubstituted, monosubstituted, or disubstituted nitrogen, including cyclic structures.

Subunits C–E in FIG. 1 are designed for 7-atom unit-length backbones as shown for C—C through E—E in FIG. 2. In Structure C, the X moiety is as in Structure B and the moiety Y may be a methylene, sulfur, or preferably oxygen. In Structure D the X and Y moieties are as in Structure B. In Structure E, X is as in Structure B and Y is O, S, or NR. In all subunits depicted in FIGS. 1A–E, Z is O or S, and $P_i$ or $P_j$ is adenine, cytosine, guanine or uracil.

As used herein, a "morpholino oligomer" refers to a polymeric molecule having a backbone which supports bases capable of hydrogen bonding to typical polynucleotides, wherein the polymer lacks a pentose sugar backbone moiety, and more specifically a ribose backbone linked by phosphodiester bonds which is typical of nucleotides and nucleosides, but instead contains a ring nitrogen with coupling through the ring nitrogen. A preferred "morpholino" oligonucleotide is composed of morpholino subunit structures of the form shown in FIG. 2B, where (i) the structures are linked together by phosphorous-containing linkages, one to three atoms long joining the morpholino nitrogen of one subunit to the 5' exocyclic carbon of an adjacent subunit, and (ii) $P_i$ and $P_j$ are purine or pyrimidine base-pairing moieties effective to bind, by base-specific hydrogen bonding, to a base in a polynucleotide.

This preferred aspect of the invention is illustrated in FIG. 2B, which shows two such subunits joined by a phosphorodiamidate linkage. Morpholino oligonucleotides (including antisense oligomers) are detailed, for example, in co-owned U.S. Pat. Nos. 5,698,685, 5,217,866, 5,142,047, 5,034,506, 5,166,315, 5,185, 444, 5,521,063, and 5,506,337, all of which are expressly incorporated by reference herein.

As used herein, a "nuclease-resistant" oligomeric molecule (oligomer) is one whose backbone is not susceptible to nuclease cleavage of a phosphodiester bond. Exemplary nuclease resistant antisense oligomers are oligonucleotide analogs, such as phosphorothioate and phosphate-amine DNA (pnDNA), both of which have a charged backbone, and methyl-phosphonate, morpholino, and peptide nucleic acid (PNA) oligonucleotides, all of which may have uncharged backbones.

As used herein, an oligonucleotide or antisense oligomer "specifically hybridizes" to a target polynucleotide if the oligomer hybridizes to the target under physiological conditions, with a Tm substantially greater than 37° C., preferably at least 50° C., and typically 60° C.–80° C. or higher. Such hybridization preferably corresponds to stringent hybridization conditions, selected to be about 10° C., and preferably about 5° C. lower than the thermal melting point ($T_{[m]}$) for the specific sequence at a defined ionic strength and pH. At a given ionic strength and pH, the $T_{[m]}$ is the temperature at which 50% of a target sequence hybridizes to a complementary polynucleotide.

Polynucleotides are described as "complementary" to one another when hybridization occurs in an antiparallel configuration between two single-stranded polynucleotides. A double-stranded polynucleotide can be "complementary" to another polynucleotide, if hybridization can occur between one of the strands of the first polynucleotide and the second. Complementarity (the degree that one polynucleotide is complementary with another) is quantifiable in terms of the proportion of bases in opposing strands that are expected to form hydrogen bonds with each other, according to generally accepted base-pairing rules.

As used herein the term "analog" with reference to an oligomer means a substance possessing both structural and chemical properties similar to those of a reference oligomer.

As used herein, a first sequence is an "antisense sequence" with respect to a second sequence if a polynucleotide whose sequence is the first sequence specifically binds to, or specifically hybridizes with, the second polynucleotide sequence under physiological conditions.

As used herein, a "base-specific intracellular binding event involving a target RNA" refers to the sequence specific binding of an oligomer to a target RNA sequence inside a cell. For example, a single-stranded polynucleotide can specifically bind to a single-stranded polynucleotide that is complementary in sequence.

As used herein, "nuclease-resistant heteroduplex" refers to a heteroduplex formed by the binding of an antisense oligomer to its complementary target, which is resistant to in vivo degradation by ubiquitous intracellular and extracellular nucleases.

As used herein, the term "target", relative to an mRNA or other nucleic acid sequence, refers to an mRNA or other nucleic acid sequence which is preferentially expressed in hematopoietic stem cells. Preferentially expressed means the target mRNA is derived from a gene expressed in hematopoietic stem cells to a greater extent than the same gene is expressed in more differentiated cells, or expression specific to hematopoietic stem cells and not detectable in more differentiated cells.

As used herein, the term "modulating expression" relative to oligonucleotides refers to the ability of an antisense oligomer to either enhance or reduce the expression of a given protein by interfering with the expression, or translation of RNA. In the case of enhanced protein expression, the antisense oligomer may block expression of a suppressor gene, e.g., a tumor suppressor gene. In the case of reduced protein expression, the antisense oligomer may directly block expression of a given gene, or contribute to the accelerated breakdown of the RNA transcribed from that gene.

As used herein, the terms "tumor" and "cancer" refer to a cell that exhibits a loss of growth control and forms unusually large clones of cells. Tumor or cancer cells generally have lost contact inhibition and may be invasive and/or have the ability to metastasize.

As used herein, "effective amount" relative to an antisense oligomer refers to the amount of antisense oligomer administered to a mammalian subject, either as a single dose or as part of a series of doses, that is effective to inhibit expression of a selected target nucleic acid sequence.

As used herein "treatment" of an individual or a cell is any type of intervention used in an attempt to alter the natural course of the individual or cell. Treatment includes, but is not limited to, administration of e.g., a pharmaceutical composition, and may be performed either prophylactically, or subsequent to the initiation of a pathologic event or contact with an etiologic agent.

As used herein, the term "improved therapeutic outcome" relative to a cancer patient refers to a slowing or diminution of the growth of cancer cells or a solid tumor, or a reduction in the total number of cancer cells or total tumor burden.

II. Antisense Oligonucleotides

The antisense oligonucleotide agents of the invention comprise nucleotide subunits joined by internucleotide backbone linkages which present the nucleotide bases for hybridization with target mRNA sequences. The base sequences of these agents are complementary (antisense) to portions of an mRNA which is preferentially expressed in hematopoietic stem cells. Preferentially expressed means the target mRNA is derived from a gene expressed in hematopoietic stem cells to a greater extent than the same gene is expressed in more differentiated cells, or expression which is specific to hematopoietic stem cells and not detectable in more differentiated cells.

A. Types of Antisense Oligonucleotides

Antisense oligonucleotides of 15–20 bases are usually long enough to have one complementary sequence in the mammalian genome. In addition, antisense compounds having a length of at least 17 nucleotides in length have been demonstrated to hybridize well with their target mRNA (Cohen, et al., 1991).

Two general mechanisms have been proposed to account for inhibition of expression by antisense oligonucleotides. (See e.g., Agrawal, et al., 1990; Bonham, et al., 1995; and Boudvillain, et al., 1997).

In the first, a heteroduplex formed between the oligonucleotide and mRNA is a substrate for RNase H, leading to cleavage of the mRNA. Oligonucleotides belonging, or proposed to belong, to this class include phosphorothioates, phosphotriesters, and phosphodiesters (unmodified "natural" oligonucleotides). Such compounds generally show high activity, and phosphorothioates are currently the most widely employed oligonucleotides in antisense applications. However, these compounds tend to produce unwanted side effects due to non-specific binding to cellular proteins (Gee, et al., 1998), as well as inappropriate RNase cleavage of non-target RNA heteroduplexes (Giles, et al., 1993).

A second class of oligonucleotide analogs, termed "steric blockers" or, alternatively, "RNase H inactive" or "RNase H resistant", have not been observed to act as a substrate for RNase H, and are believed to act by sterically blocking target RNA formation, nucleocytoplasmic transport, or translation. This class includes methylphosphonates (Toulme, et al., 1996), morpholino oligonucleotides, peptide nucleic acids (PNA's), 2'-O-allyl or 2'-Oalkyl modified oligonucleotides (Bonham, 1995), and N3' P5' phosphoramidates (Gee, 1998).

Naturally occurring oligonucleotides have a phosphodiester backbone which is sensitive to degradation by nucleases, however, certain modifications of the backbone increase the resistance of native oligonucleotides to such degradation. (See, e.g., Spitzer and Eckstein 1988).

Candidate antisense oligomers are evaluated, according to well known methods, for acute and chronic cellular toxicity, such as the effect on protein and DNA synthesis as measured via incorporation of $^3$H-leucine and $^3$H-thymidine, respectively. In addition, various control oligonucleotides, e.g., control oligonucleotides such as sense, nonsense or scrambled antisense sequences, or sequences containing mismatched bases, in order to confirm the specificity of binding of candidate antisense oligomers. The outcome of such tests are important to discern specific effects of antisense inhibition of gene expression from indiscriminate suppression. (See, e.g. Bennett, et al., 1995). Accordingly, sequences may be modified as needed to limit non-specific binding of antisense oligomers to non-target sequences.

The effectiveness of a given antisense oligomer molecule in forming a heteroduplex with the target RNA may be determined by screening methods known in the art. For example, the oligomer is incubated a cell culture expressing c-myc, and the effect on the target RNA is evaluated by monitoring the presence or absence of (1) heteroduplex formation with the target sequence and non-target sequences using procedures known to those of skill in the art, (2) the amount of target mRNA, as determined by standard techniques such as RT-PCR or Northern blot, or (3) the amount of target protein, as determined by standard techniques such as ELISA or Western blotting. (See, for example, Pari, et al., 1995; Anderson, et ol., 1996).

Exemplary antisense oligomers for use in the methods of the invention include morpholino oligomers (FIGS. 2A–D), peptide nucleic acids and methyl phosphonate oligomers.

1. Morpholino Antisense Oligonucleotides

Preferred antisense oligonucleotides are nuclease-resistant oligomers with substantially uncharged backbones, and particularly morpholino oligomers having, in addition to a base sequence complementary to a region of a selected mRNA target sequence, an oligomer backbone, defined by the nucleotide subunits of the oligomer and the linkages between them such that the oligomer can bind the target RNA sequence by Watson-Crick base pairing between complementary bases in the target RNA and the oligomer.

The synthesis, structures, and binding characteristics of morpholino oligomers are detailed in U.S. Pat. Nos. 5,698,685, 5,217,866, 5,142,047, 5,034,506, 5,166,315, 5,521,063, and 5,506,337, each of which is expressly incorporated by reference herein.

The preferred oligomers are composed of morpholino subunits of the form shown in the above cited patents, where (i) the morpholino groups are linked together by substantially uncharged linkages, one to three atoms long, joining the morpholino nitrogen of one subunit to the 5' exocyclic carbon of an adjacent subunit, and (ii) the base attached to the morpholino group is a purine or pyrimidine base-pairing moiety effective to bind, by base-specific hydrogen bonding, to a base in a polynucleotide. The purine or pyrimidine base-pairing moiety is typically adenine, cytosine, guanine, uracil or thymine. Preparation of such oligomers is described in detail in U.S. Pat. No. 5,185,444 (Summerton and Weller, 1993), which is hereby incorporated by reference in its entirety. A variety of types of nonionic linkages may be used to construct a morpholino backbone. Morpholino oligomers exhibit little or no non-specific antisense activity, afford good water solubility, are immune to nucleases, and are designed to have low production costs (Summerton and Weller, 1997b).

2. Peptide Nucleic Acids (PNAs)

It has been demonstrated that the phosphodiester backbone found in naturally occurring oligonucleotides is not essential for a potent structural DNA mimic and not even required for a helical duplex structure, and that peptide or protein nucleic acids (PNAs), may function as effective DNA mimics (Nielsen, 1995).

PNAs are analogs of DNA in which the backbone is structurally homomorphous with a deoxyribose backbone. It consists of N-(2-aminoethyl)glycine units to which pyrimidine or purine bases are attached. PNAs containing natural pyrimidine and purine bases hybridize to complementary oligonucleotides obeying Watson-Crick base-pairing rules, and mimic DNA in terms of base pair recognition (Egholm et al., 1993). The backbone of PNAs are formed by peptide bonds rather than phosphodiester bonds, making them well-suited for antisense applications. The backbone is uncharged, resulting in PNA/DNA or PNA/RNA duplexes which exhibit greater than normal thermal stability. PNAs are not recognized by nucleases or proteases. However, PNA antisense agents has been observed to display slow membrane penetration in cell cultures, possibly due to poor uptake (transport) into cells. (See, e.g., Ardhammar M et al., 1999).

3. Methylphosphonate Oligonucleotides

Methylphosphonate oligonucleotides are uncharged and therefore predicted to exhibit enhanced cellular uptake relative to charged oligonucleotides (Blake, et al., 1985). However, methylphosphonate antisense oligomers have been shown to be incapable of inhibiting N-ras expression in vitro (Tidd, et al, 1988). In contrast, in vitro translation of several oncogene mRNAs was shown to be successfully blocked by phosphodiester and/or phosphorothioate antisense oligonucleotides (c-myc: McManaway, et al., 1990; Watson, et al., 1991; bcl-2: Reed, et al., 1990; myb: Calabrett, et al., 1991; bcr-ab: Szczylik, et al., 1991). The synthesis of methyl phosphonate oligomers requires multiple steps which may limit the practical utility of the use of such structure in clinical applications.

4. Preferred Antisense Oligomers mRNA transcribed from the relevant region of a gene of interest is generally targeted by antisense oligonucleotides, however, in some cases double-stranded DNA may be targeted using a non-ionic probe designed for sequence-specific binding to major-groove sites in duplex DNA. Such probe types are described in U.S. Pat. No. 5,166,315 (Summerton and Weller, 1992), which is hereby incorporated by reference, and are generally referred to herein as antisense oligomers, referring to their ability to block expression of target genes.

In the methods of the invention, the antisense oligomer is designed to hybridize to a region of an RNA sequence preferentially expressed in stem cells, e.g., HSC, under physiological conditions with a Tm substantially greater than 37° C., e.g., at least 50° C. and preferably 60° C.–80° C. The oligomer is designed to have high-binding affinity to the nucleic acid and may be 100% complementary to the target sequence, or may include mismatches, e.g., to accommodate allelic variants, as long as the heteroduplex formed between the oligomer and the target sequence is sufficiently stable to withstand the action of cellular nucleases and other modes of degradation during its transit from cell to body fluid. Mismatches, if present, are less destabilizing toward the end regions of the hybrid duplex than in the middle. The number of mismatches allowed will depend on the length of the oligomer, the percentage of G:C base pair in the duplex and the position of the mismatch(es) in the duplex, according to well understood principles of duplex stability.

Although such an antisense oligomer is not necessarily 100% complementary to the target sequence, it is effective to stably and specifically bind to the target sequence such that expression of the target is modulated. The appropriate length of the oligomer to allow stable, effective binding combined with good specificity is about 8–40 nucleotide base units, and preferably about 12–25 nucleotides. Oligomer bases that allow degenerate base pairing with target bases are also contemplated, assuming base-pair specificity with the target is maintained.

In general, the target for modulation of gene expression using the antisense methods of the present invention comprises an mRNA preferentially expressed in stem cells. However, in some cases, other regions of the mRNA may be targeted, including one or more of, an initiator or promoter site, an intron or exon junction site, a 3'-untranslated region, and a 5'-untranslated region. In addition, both spliced and unspliced RNA may serve as the template for design of 1 antisense oligomers for use in the methods of the invention.

As noted above, the antisense oligomers of the invention generally have a sequence which spans the start codon of an mRNA preferentially expressed in stem cells, meaning the compound contains a sequence complementary to a region of the target RNA containing the AUG mRNA start site and adjacent 5' and 3' base(s). The region of the mRNA against which the compound is directed is also referred to herein as the target sequence. The mRNA to which the antisense binds may be preprocessed (prespliced) mRNA, in which case the antisense compound may act to interfere with correct splicing, leading to truncated forms of the translated protein, or may bind to the processed mRNA, leading to inhibition of translation. In summary, preferred antisense oligomers for use in the methods of the invention preferably, have one or more properties including: (I) a backbone which is substantially uncharged (e.g., Uhlmann, et al., 1990), (2) the ability to hybridize with the complementary sequence of a target RNA with high affinity, that is, Tm substantially greater than 37° C., preferably at least 50° C., and typically 60° C.–80° C. or higher, (3) a subunit length of at least 8 bases, generally about 840 bases, preferably 12–25 bases, (4) nuclease resistance (Hudziak, et al., 1996) and (5) capable of active or facilitated transport as evidenced by (i) competitive binding with a phosphorothioate antisense oligomer, and/or (ii) the ability to transport a detectable reporter into the cells.

In a preferred aspect, the antisense oligomer comprises a sequence selected from the group consisting of SEQ ID NO:1 through SEQ ID NO:7, and SEQ ID NO:10 through SEQ ID NO:12, as further described below.

III. Hematopoietic Stem Cell Compositions

A. Methods of Obtaining Hematopoietic Stem Cells

In adults, the large majority of pluripotent hematopoietic stem cells are found in the bone marrow. However, small but significant numbers of such cells can be found in the peripheral circulation, liver and spleen.

Hematopoietic stem cells for use in the methods of the invention may be derived from human bone marrow, human newborn cord blood, fetal liver, or adult human peripheral blood after appropriate mobilization.

The frequency of hematopoietic stem cells can be dramatically increased by treatment of a subject with certain compounds including cytokines. Such "mobilized" peripheral blood hematopoietic stem cells have become an important alternative to bone marrow-derived hematopoietic stem cells in transplantation procedures primarily because engraftment is more rapid. (See, e.g., Tanaka, et al., 1999). Such mobilization may be accomplished using for example, one or more of granulocyte colony-stimulating factor (G-CSF), stem cell factor (SCF), thrombopoietin (TPO), and a chemotherapeutic agent (i.e., cyclophosphamide).

Numerous methods for hematopoictic stem cell isolation are known in the art and generally include obtaining hematopoietic stem cells from bone marrow, newborn cord blood, fetal liver or adult human peripheral blood. Once obtained, a hematopoietic stem cell population is enriched by performing one or more of a density gradient separation, immunoaffinity purification using positive and/or negative selection by techniques such as panning, FACS and magnetic bead separation. Following such enrichment steps, the cell population is further characterized phenotypically and functionally.

Previous studies have demonstrated that primitive hematopoietic cells, characterized as high proliferative potential colony-forming cells (HPP-CFC, in vitro) may be isolated by selecting a fraction of density gradient-enriched, lineage-depleted marrow cells; and further selecting a cell population based on a single step fluorescence-activated cell sorter (FACS) fractionation for cells that bind low levels of the DNA binding dye, Hoechst 33342 and low levels of the mitochondrial binding dye, Rhodamine 123 (Wolf, et al., 1993). Recently, it has been shown that a defined subpopulation of HPP-CFC are transplantable and that a subpopulation of the cells that give rise to HPP-CFC are LTR-HSCs, which can replicate ex vivo. (See, e.g., Yagi, et al, 1999).

B. Characterization of Hematopoietic Stem Cell Compositions

Hematopoietic stem cells have been historically defined as transplantable cells, capable of self-renewal as well as possessing the ability to generate daughter cells of any hematopoietic lineage. Lineage-committed progenitor cells are defined as more differentiated cells derived from hematopoietic stem cells.

The phenotypic markers which characterize the hematopoietic stem cell have been the subject of extensive debate and numerous publications. As yet, there is no consensus as to which markers are definitive for murine or human hematopoietic stem cells.

LTR-HSC have been isolated and characterized in mice herein using fluorescence-activated cell sorter (FACS) selection of density gradient-enriched, lineage-depleted bone marrow cells that are negative for expression of the CD34 antigen, positive for expression of the CD 117 (c-kit) antigen, and exhibit low-level binding of the DNA binding dye, Hoechst 33342 (Ho-33342) and the mitochondrial binding dye, Rhodamine 123 (Rh-123), (Wolf, et al., 1993). This isolated cell population has been demonstrated to be transplantable and capable of repopulating lethally irradiated recipients when transplanted together with unfractionated bone marrow cells.

The STR-HSC population may be selected by FACS sorting and is phenotypically defined herein as light density gradient-enriched bone marrow cells which lack the expression of lineage markers (lin−), are positive for c-kit (CD 117), Sca1 and CD34, exhibit low-level binding of the DNA binding dye, Hoechst 33342 (Ho-33342) and high-level binding of the mitochondrial binding dye, Rhodamine 123 (Rh-123).

Functional readouts that have been used to detect and characterize hematopoietic stem cells include the ability to form colonies under particular assay conditions in cell culture (in vitro). Exemplary assays include the long term culture initiating cell (LTCIC) assay (Pettengell R et al., 1994), and the high proliferative potential-colony-forming cell (HPP-CFC) assay. (See, e.g., Yagi, et al., 1999.) Further functional characterization includes in vivo assay for long-term repopulating hematopoietic stem cells (LTR-HSC) and short-term repopulating hematopoietic stem cells (STR-HSC), as described above.

Hematopoietic stem cells are often functionally characterized by activity in the high proliferative potential colony-forming cell (HPP-CFC) assay, as defined above.

HPP-CFC have been characterized by: (1) a relative resistance to treatment in vivo with the cytotoxic drug 5-fluorouracil; (2) high correlation with cells capable of repopulating the bone marrow of lethally irradiated mice; (3) their ability to generate cells of the macrophage, granulocyte, megakaryocyte and erythroid lineages under appropriate conditions; and (4) their multifactor responsiveness. (See, e.g., McNiece, 1990).

Hematopoietic stem cells for use in the methods of the invention are enriched, as described in Example I. The cells were also characterized functionally in the HPP-CFC assay (in vitro) and in an assay for LTR-HSCs (in vivo), as further described in Example 2.

Preferred cytokines for the culture of hematopoietic stem cells include one or more of interleukin-3 (IL-3), interleukin-6 (IL-6), interleukin-11 (IL-11), interleukin-12 (IL-12), stem cell factor (SCF), an early acting hematopoietic factor, described, for example in WO 91/05795, and thrombopoietin (TPO).

Long-term reconstitution with murine LTR-HSCs following complete immunosuppression has been shown to require the transplantation of unfractionated bone marrow cells together with less differentiated long term repopulating cells, in order to provide initial, albeit unsustained engraftment, which allows the completely immunosuppressed host to survive until the long term repopulating cells differentiate sufficiently to repopulate the host. (See, e.g., Jones, et al., 1990). LTR-HSCs may take several months to effectively repopulate the hematopoietic system of the host following complete immunosuppression.

Methods have been developed to distinguish the cells of the donor and recipient in murine hematopoietic reconstitution studies, by using donor hematopoietic stem cells, congenic at the CD45 locus, defined as CD45.1 and recipient hemalopoietic stem cells defined as CD45.2, such that monoclonal antibodies may be used to distinguish donor and recipient cells, ie. by FACS analysis and/or sorting. In such detection methods, the recipient is infused with sufficient CD45.2 positive bone marrow cells to keep the mouse alive until differentiation of CD45.1 donor cells occur to an extent sufficient to repopulate the hematopoietic system of the recipient. Such methods may be used to differentiate LTR-HSCs from STR-HSCs, and donor cells from recipient cells.

Once a hematopoietic stem cell population is obtained, the cells may be used immediately or frozen in liquid nitrogen and stored for long periods of time, under standard conditions, such that they can later be thawed and used, e.g., for administration to a patient. The cells will is usually be stored in 10% DMSO, 50% fetal calf serum (FCS), and 40% cell culture medium.

IV. Nucleic Acid Targets

The invention generally relates to synthetic antisense oligonucleotides directed against a human gene associated with cellular development or differentiation and methods employing the same. In particular, the invention relates to antisense oligonucleotides directed against an mRNA transcribed from a human gene associated with differentiation of stem cells, preferably hematopoietic stem cells (HSC).

Exemplary genes expressed in stem cells to a greater extent than in more developed cells were identified by representational differential analysis (RDA) and gene expression fingerprinting (GEF) using techniques routinely employed by those of skill in the art, as further described in Example 1. (See, e.g., Matz M V and Lukyanov S A, *Nucleic Acids Res* 26(24):5537–43, 1998.)

Preferred antisense targets for practicing the present invention include transcripts that are preferentially expressed in stem cells, for example, the EVI-1 zinc finger gene, the serum-deprivation response gene, the multimerin gene, the tissue transglutaminase gene, the FE65 gene, the RAB27 gene, the Jagged2 gene, the Notch1 gene, the Notch2 gene and the Notch3 gene. Of particular interest are those sequences preferentially expressed in human hematopoietic stem cells.

In general, targets for modulation of gene expression using the antisense oligomers of the present invention comprise a sequence spanning the mRNA translational start codon for a given gene of interest. However, in some cases, other regions of the mRNA may be targeted, including one or more of, an initiator or promoter site, an intron or exon junction site, a 3'-untranslated region, and a 5'-untranslated region. In addition, both spliced and unspliced RNA may serve as the target for the antisense oligomers described herein.

Zinc-finger protein-encoding genes have been shown to participate in the control of cell proliferation and differentiation, and accordingly are candidate oncogenes. Zinc-finger genes, such as EVI-1, have been associated with a variety of tumor types, including mouse and human myeloid leukemia (Morishita, et al. 1998; Fichelson, et al., 1992). Terminal differentiation of hematopoietic cells has also been associated with the down-regulation of zinc-finger gene expression. The EVI-1 gene was originally detected as an ectopic viral insertion site and encodes a nuclear zinc finger DNA-binding protein. The EVI-1 gene is overexpressed in hematopoietic malignancies including some leukemias and lymphomas. (Ohyashiki, et al., 1994; Toyama, et al., 1996). In addition, EVI-1 RNA or protein expression has been detected in: a kidney cell line; an endometrial carcinoma cell line; normal murine oocytes; kidney cells; a subset of acute myeloid leukemia's (ALMs) and myelodysplasia; ovarian tumors, normal ovaries and ovarian cell lines; Ewing's Sarcoma, a genetically inherited disease; and a variety of other non-hematological cancers. (See, e.g., Brooks, et al., 1996). It has been suggested that EVI-1 is a relevant oncogene whose overexpression, constitutive expression or structural changes may play a role in the development of human leukemias (Ogawa, et al., 1996).

An exemplary oligomer antisense to EVI-1 for use in practicing the invention is presented as SEQ ID NO:1 and was designed based on the sequences found at GenBank Accession Nos. S69002 (human, nucleotides 2650–2670) and MMEV11A (murine, nucleotides 256–276).

The human serum deprivation response gene (SDR) which encodes a phosphatidylserine-binding protein, has been cloned and mapped to 2q32-q33 in the human genome (Gustincich, et al., 1999). Analogous to the murine system, in vitro SDR mRNA expression is increased in serum starved human fibroblasts and becomes down-regulated during synchronous cell-cycle reentry. SDR is expressed in a wide variety of human tissues, with highest levels found in heart and lung.

An exemplary oligomer antisense to SDR for use in practicing the invention is presented as SEQ ID NO:2 and was designed based on the sequence found at Gen Bank Accession No. S67386 (murine, nucleotides 109–128).

Multimerin is a high molecular weight protein with a unique cDNA sequence, which is stored in platelets, megakaryocytes and endothelial cells, and appears to function as an adhesive or extracellular matrix protein. Multimerin undergoes extensive N-glycosylation, proteolytic processing and polymerization during biosynthesis and is comprised of subunits linked by interchain disulfide bonds to form large, variably sized homomultimers (Hayward, and Kelton, 1995; Hayward 1997).

An exemplary oligomer antisense to multimerin for use in practicing the invention is presented as SEQ ID NO:3 and was designed based on the sequence found at GenBank Accession No. U27109 (human, nucleotides 60–80).

Tissue transglutaminase is an enzyme induced and activated during apoptosis, which has been shown to convert latent TGF-beta to the active form (Nunes et al, 1997) and has been associated with Ca(2+)-dependent cross-linking of intracellular proteins leading to the formation of an SDS-insoluble protein scaffold in cells undergoing programmed cell death. When antibodies were used to block autocrine, surface expressed TGF-beta on HSC, the cells were found to survive in the absence of growth factors. It has also been shown that transfection of human cells with the cDNA for tissue transglutaminase in an antisense orientation results in a decrease in spontaneous and induced apoptosis (Autuori, et al., 1998).

An exemplary oligomer antisense to transglutaminase for use in practicing the invention is presented as SEQ ID NO:4 and was designed based on the sequence found at GenBank Accession No. S81734 (human, nucleotides 123–142).

FE65 is a brain-enriched protein that binds to the Alzheimer's beta amyloid protein precursor (APP), which following proteolytic processing is converted to Abeta, the principal component of Alzheimer's amyloid plaques. It has been suggested that agents which inhibit the interaction of FE65 with APP might prevent or slow amyloid plaque formation (Sabo, 1999; Russo, 1998.

An exemplary oligomer antisense to FE65 for use in practicing the invention is presented as SEQ ID NO:5 and was designed based on the sequence found at GenBank Accession No. L77864 (human, nucleotides 92–111).

The RAB27 gene encodes a cytosolic protein, identified as Ram (renamed Rab27), which is a prenylated member of a family of GTP-binding proteins that serve as membrane anchors and determinants of specific protein:protein interactions (Nagata, 1989). They have been shown to regulate vesicular traffic in the secretory and endocytic pathways in platelets, melanocytes, and certain other tissue and have been found to be associated with retinal degeneration in choroideremia (Seabra, et al., 1995).

An exemplary oligomer antisense to RAB27 for use in practicing the invention is presented as SEQ ID NO:6 and was designed based on the sequence found at GenBank Accession No. AF125393 (human, nucleotides 227–246).

The Notch signaling pathway has been implicated in the control of cellular differentiation in animals ranging from nematodes to humans. Studies have indicated that the Jagged2 gene encodes a membrane-bound receptor that interacts with Notch1 and may function in vivo to coordinate differentiation of progenitor cells (Luo, et al., 1997). In humans, notch signaling has also been implicated in leukemia and two hereditary syndromes known as Alagille and CADASIL. Notch ligand, including human Jagged2 (HJ2) have been found to be unregulated in certain neoplastic tissues (Gray, et al., 1999).

An exemplary oligomer antisense to Jagged2 for use in practicing the invention is presented as SEQ ID NO:7 and was designed based on the sequence found at GenBank Accession No. AF003521 (human: nucleotides 22–41).

Members of the Notch gene family have been shown to mediate cell-fate decisions by multipotent precursors in a number of systems. It has been demonstrated that TAN-I (Notch 1), is expressed in CD34+hematopoietic precursors. (See, e.g., Milner L A et al., 1994 and Milner L A and Bigas A, 1999.)

Exemplary oligomers antisense to Notch2, Notch3 and Notch1, respectively (SEQ ID NO:10, SEQ ID NO:11 and SEQ ID NO:12), for use in practicing the invention were designed based on the sequences found at GenBank Accession Nos. X80115 and X79439 (human: nucleotides 215–235 and nucleotides 1–20) and GenBank Accession No. AJ238029 (murine: nucleotides 231–250). An exemplary human Notch1 oligomer for use in practicing the invention may be designed based on the sequence found at GenBank Accession No. M73980.

V. Methods and Compositions of the Invention

The invention is based on the discovery that a stable, substantially uncharged antisense oligonucleotide, characterized by high Tm, capable of active or facilitated transport into cells, and capable of binding with high affinity to a complementary or near-complementary nucleic acid sequence which is preferentially expressed in stem cells, can be administered to a stem cell, and modulate expression of the target sequence in the cell, either in vitro, or in vivo in a subject, resulting in modified development of the cell. In one preferred approach, the target is a sequence spanning the mRNA translational start codon for an mRNA preferentially expressed in stem cells, preferably HSC.

Many cancer treatment regimens result in immunosuppression of the patient, leaving the patient unable to defend against infection. Supportive care for immunosuppression may include protective isolation of the patient such that the patient is not exposed to infectious agents; administration of: antibiotics, e.g., antiviral agents and antifungal agents; and/or periodic blood transfusions to treat anemia, thrombocytopenia (low platelet count), or neutropenia (low neutrophil count).

Transplantation of hematopoietic stem cells derived from peripheral blood and/or bone marrow is increasingly used in combination with chemotherapy and/or radiation therapy for the treatment of a variety of disorders including numerous forms of cancer.

Current transplantation regimens that employ cell populations enriched for hematopoietic stem cells and/or bone marrow transplantation also suffer from an excessive lag time between transplantation and repopulation of the patient's hematopoietic system, in particular patients often suffer from a deficiency in neutrophils and platelets.

Neutrophils are involved in defending the host against infection. Frequently, following a chemotherapy or radiation therapy, a patient will suffer from insufficient neutrophil counts for time period of from about 3 to 4 weeks, or a longer time period resulting in increased susceptibility to infection.

Platelets are necessary for effective blood clotting at a site of injury. Frequently, following chemotherapy, radiation therapy, transplantation of a cell population enriched for hematopoietic stem cells or bone marrow transplantation, a patient will suffer from an insufficient platelet count for a time period of from about 4 to 6 weeks, or a longer time period resulting in the patient being easily bruised and excessive bleeding.

In preferred applications of the method, the subject is a human subject. The subject may be a cancer patient, in particular a patient diagnosed as having a hematopoietic malignancy, particularly a malignancy characterized by expansion or dysfunction of pluripotent hematopoietic stem cells, for example, chronic myelocytic leukemia (CML), polycythemia vera (PV), primary myelofibrosis (MF), aplastic anemia, essential thrombocythemia (ET) and various other types of leukemia. The present invention provides a means to the number of lineage committed progenitor cells and their progeny in the peripheral circulation of the subject.

In addition, the invention is applicable to treatment of any condition wherein promoting the differentiation of stem cells would be effective to result in an improved therapeutic outcome for the subject under treatment.

A. Treating Cells Ex Vivo with Antisense Oligomers

Hematopoietic stem cells may be obtained from a patient in need of transplantation, e.g., a cancer patient; enriched, treated in vitro (ex vivo) using the methods described herein, and returned to the patient. In general, such hematopoietic stem cell transplantation is carried out in conjunction with typical therapeutic regimens, i.e., radiation and/or chemotherapy.

In practicing the method, hematopoietic stem cells may be treated in vitro (ex vivo) with one or more oligonucleotide antisense to a nucleic acid sequence that is preferentially expressed in stem cells, followed by administration to a subject. The subject may be the same individual from whom the stem cells were obtained (autologous transplantation) or a different individual (allogeneic transplantation). In allogeneic transplantation, the donor and recipient are matched based on similarity of HLA antigens in order to minimize the immune response of both donor and recipient cells against the other.

In one aspect, the invention is directed to methods of modifying the development of hematopoietic stem cells, by obtaining a population of HSCs and exposing them ex vivo to one or more nuclease-resistant antisense oligomers having high affinity to a complementary or near-complementary nucleic acid sequence preferentially expressed in stem cells.

The methods of the invention are effective to produce more differentiated cells (i.e., lineage committed progenitor cells and their progeny) such as monocytes, granulocytes, platelets, lymphocytes and red blood cells, by exposing a hematopoietic stem cell to one or more of the antisense oligomers described herein, under conditions suitable to promote differentiation of the stem cell to a more mature phenotype. Such antisense oligonucleotide-treated stem cells find utility in the treatment of cancer upon reinfusion into a subject.

In a related aspect, the antisense oligonucleotides of the invention can be used to obtain an increased number of viable cells of a particular lineage in vitro (ex vivo), for subsequent in vivo administration to a patient. In general stem cells are cultured in medium containing the one or more antisense oligonucleotides of the invention together with one or more growth factors effective to promote growth and differentiation of a target cell population.

In one preferred embodiment, ex vivo antisense oligomer, e.g., EVI-1-treated hematopoietic stem cells are infused into a patient and provide a means to rapidly increase the number of both neutrophils and platelets in the circulation of the patient following chemotherapy or radiation therapy.

In one aspect, once extracted and enriched, stem cells, e.g., HSC, may be cultured ex vivo in the presence of one or more cytokines and one or more antisense oligomers described herein. Such an antisense oligomer-treated hematopoietic stem cell composition finds utility in a variety of applications, including, but not limited to, expanding or multiplying the population (i.e., number) of particular lineage-committed progenitor cells and their progeny ex vivo for subsequent in vivo administration to a subject, and inhibiting or arresting growth of cancer cells wherein the cancer is associated with the hematopoietic stem cell population.

Preferred cytokines for such ex vivo culture include IL-3, IL-6, SCF and TPO. A hematopoietic stem cell population for use in the methods of the invention is preferably both human and allogeneic, or autologous.

Hematopoietic stem cells may be obtained from a patient in need of hematopoietic stem cell transplantation or from an allogeneic donor.

In one approach, the method of the invention results in an increase in the number of viable differentiated cells, e.g., monocytes, granulocytes, platelets, lymphocytes and red blood cells which is at least 2-fold greater than the number of hematopoietic stem cells present prior to exposure to the antisense oligomer. Exemplary antisense oligomers are target one or more of an EVI-1 zinc finger gene, a serum deprivation response (SDR) gene, a multimerin gene, a tissue transglutaminase gene, an FE65 gene, a RAB27 gene, a Jagged2 gene, a Notch1 gene, a Notch2 gene and a Notch3 gene.

Preferably, the exposure of hematopoietic stem cells to one or more antisense oligomers of the invention using the methods described herein results in a differentiated cell population that is increased at least 4-fold to 8-fold and preferably 8-fold or more relative to the number of lineage committed progenitor cells and their progeny in the peripheral circulation of the subject prior to exposure to the antisense oligomer.

In a preferred aspect of this embodiment, the treatment of stem cells, e.g. HSC, with one or more antisense oligomers of the invention results in an increase in the number of cells of a particular lineage which is at least 4-fold to 8-fold and preferably 8-fold or more relative to the number of cells of that particular lineage present prior to exposure to the antisense oligomer.

The culture time required to obtain at least a 2-fold, 4-fold, 8-fold, or greater than 8-fold increase in the number of differentiated and committed progenitor cells (e.g., monocytes, granulocytes, platelets, lymphocytes and red blood cells), following exposure to one or more antisense oligonucleotides (as described herein) will vary dependent upon a number of factors. Exemplary factors which may affect the number and quality of cells produced include the cell source (including the tissue source and the health of the subject from whom the cells were taken), culture conditions, the percentage of stem cells in the starting population, etc.

In such cases, hematopoietic stem cells are obtained from a patient in need of transplantation of a particular type of cell, e.g., neutrophils, platelets, lymphocytes, erthryrocytes or monocytes.

As will be appreciated, an increase in cells of various cell lineages results from differentiation of hematopoietic stem cells. In particular, large numbers of neutrophils and platelets maybe obtained using the methods of the invention.

Once a large number of cells, i.e., cells of a particular lineage, are obtained, the cells can be used immediately or frozen in liquid nitrogen and stored for long periods of time, using standard conditions, such that they can later be thawed and used, e.g., for administration to a patient. The cells will usually be stored in 10% DMSO, 50% fetal calf serum (FCS), and 40% cell culture medium.

B. In Vivo Administration of Antisense Oligomers

In another aspect, the invention is directed to methods of modifying the development of stem cells in vivo in a patient, preferably a cancer patient, by administering to the patient a therapeutically effective amount of an antisense oligonucleotide-containing composition, where the antisense oligomer modulates the expression of a gene product preferentially expressed in stem cells.

Such in vivo antisense oligomer administration may also be effective to improve the therapeutic outcome of the subject by effecting a slowing or diminution of the growth of cancer cells or a solid tumor, or a reduction in the total number of cancer cells or total tumor burden and/or by increasing the number of lineage committed progenitor cells and their progeny in the peripheral circulation of the subject.

In one embodiment, a subject has been diagnosed with cancer. In this embodiment, one or more antisense oligomers complementary to a nucleic acid sequence preferentially expressed in hematopoietic stem cells is administered to the subject in a manner effective to result in a reduction in the total number of cancer cells or total tumor burden in the subject.

In another embodiment, a subject is in need of an increased number of differentiated hematopoietic cells, such as neutrophils and/or platelets, e.g., following chemotherapy or radiation therapy.

In this embodiment, one or more antisense oligomers complementary to a nucleic acid sequence preferentially expressed in hematopoietic stem cells is administered to the subject in a manner effective to result in an increase in the number of both neutrophils and platelets in the peripheral circulation of the subject.

In a preferred approach, the antisense oligonucleotide composition is administered at a concentration and for a period sufficient to increase the number of lineage committed progenitor cells and their progeny in the peripheral blood of the patient at least 2-fold, preferably 4-fold, more preferably 8-fold or greater than 8-fold relative to the number of lineage committed progenitor cells and their progeny present in the peripheral blood of the patient prior to administration of the antisense oligonucleotide composition. Such an increase may be in the total number of lineage committed progenitor cells and their progeny or in the number of a particular type of lineage committed progenitor cells and their progeny, e.g. neutrophils and/or platelets.

It will be understood that in vivo administration of such an antisense oligomer to a subject using the methods of the invention can provide a means to increase the population of lineage committed progenitor cells and their progeny in the peripheral circulation of the subject, and/or effect a slowing or diminution of the growth of cancer cells or a solid tumor, or a reduction in the total number of cancer cells or total tumor burden, dependent upon, (I) the duration, dose and frequency of antisense administration, (2) the one or more antisense oligomers used in the treatment; and (3) the general condition of the subject.

1. Treating Patients

Effective delivery of an antisense oligomer to the nucleic acid target is an important aspect of the methods of the invention. In accordance with the invention, such routes of antisense oligomer delivery include, but are not limited to, various systemic routes, including oral and parenteral routes, e.g., intravenous, subcutaneous, intraperitoneal, and intramuscular, as well as inhalation and transdermal delivery.

It is appreciated that any methods which are effective to deliver the oligomer to hematopoietic stem cells or to introduce the drug into the bloodstream are also contemplated.

Transdermal delivery of antisense oligomers may be accomplished by use of a pharmaceutically acceptable carrier adapted for e.g., topical administration. One example of morpholino oligomer delivery is described in PCT patent application WO 97/40854, incorporated herein by reference.

In one preferred embodiment, the oligomer is a morpholino oligomer, contained in a pharmaceutically acceptable carrier, and delivered orally. In a further aspect of this embodiment, a morpholino antisense oligonucleotide is administered at regular intervals for a short time period, e.g., daily for two weeks or less. However, in some cases the antisense oligomer is administered intermittently over a longer period of time.

Typically, one or more doses of antisense oligomer are administered, generally at regular intervals for a period of about one to two weeks. Preferred doses for oral administration are from about 1 mg oligomer/patient to about 25 mg oligomer/patient (based on an adult weight of 70 kg). In some cases, doses of greater than 25 mg oligomeripatient may be necessary. For IV administration, the preferred doses are from about 0.5 mg oligomer/patient to about 10 mg oligomer/patient (based on an adult weight of 70 kg).

The antisense compound is generally administered in an amount sufficient to result in a peak blood concentration of at least 200–400 nM antisense oligomer.

In general, the method comprises administering to a subject, in a suitable pharmaceutical carrier, an amount of an antisense agent effective to inhibit expression of a nucleic acid target sequence of interest.

It follows that an antisense oligonucleotide composition of the invention may be administered in any convenient vehicle, which is physiologically acceptable. Such an oligonucleotide composition may include any of a variety of standard pharmaceutically accepted carriers employed by those of ordinary skill in the art. Examples of such pharmaceutical carriers include, but are not limited to, saline, phosphate buffered saline (PBS), water, aqueous ethanol, emulsions such as oil/water emulsions, triglyceride emulsions, wetting agents, tablets and capsules. It will be understood that the choice of suitable physiologically acceptable carrier will vary dependent upon the chosen mode of administration.

In some instances liposomes may be employed to facilitate uptake of the antisense oligonucleotide into cells. (See, e.g., Williams, 1996; Lappalainen, et al., 1994; Uhlmann, et al., 1990; Gregoriadis, 1979.) Hydrogels may also be used as vehicles for antisense oligomer administration, for example, as described in WO 93/01286. Alternatively, the oligonucleotides may be administered in microspheres or microparticles. (See, e.g., Wu and Wu, 1987).

Sustained release compositions are also contemplated within the scope of this application. These may include semipermeable polymeric matrices in the form of shaped articles such as films or microcapsules.

It will be understood that the effective in vivo treatment regimen of antisense oligonucleotides in the methods of the invention will vary according to the frequency and route of administration as well as the condition of the subject under treatment. Accordingly, such in vivo therapy will generally require monitoring by tests appropriate to the condition being treated and a corresponding adjustment in the dose or treatment regimen in order to achieve an optimal therapeutic outcome.

The invention provides a method to produce more differentiated cells from a hematopoietic stem cell, such as monocytes, granulocytes, platelets, lymphocytes and red blood cells, by exposing a hematopoietic stem cell to the antisense oligomers described herein, under conditions suitable to promote differentiation of the hematopoietic stem cell to a more mature phenotype.

The invention further provides a means to release HSC from a resting or $G_o$ state into the cell cycle.

A therapeutic regimen may include administration of antisense oligomer-treated stem cells and/or direct administration of one or more of the antisense oligomers described herein to the subject. Such administration may be concurrent or sequential. In some cases, the patient may be further treated by one or more of chemotherapy, radiation therapy and other agents typically used by those of skill in the art to treat individuals diagnosed with the same or a similar condition. Such further treatment may be concurrent with, sequential or alternating relative to administration of antisense oligomer-treated stem cells and/or direct administration of one or more antisense oligomers to the subject.

2. Monitoring Treatment

The efficacy of a given therapeutic regimen involving the methods described herein, may be monitored, e.g., by conventional FACS assays for the phenotype of cells in the circulation of the subject under treatment in order to monitor changes in the numbers of cells of various lineages (e.g., lineage committed progenitor cells and their progeny) in the peripheral circulation of the subject in response to such treatment.

Phenotypic analysis is generally carried out using monoclonal antibodies specific to the cell type being analyzed, e.g., neutrophils, platelets, lymphocytes, erthryrocytes or monocytes. The use of monoclonal antibodies in such phenotypic analyses is routinely employed by those of skill in the art for cellular analyses. Monoclonal antibodies specific to particular cell types are commercially available.

Hematopoietic stem cells are characterized phenotypically as detailed above. Such phenotypic analyses are generally carried out in conjunction with biological assays for each particular cell type of interest, for example (1) hematopoietic stem cells (LTCIC, cobblestone forming assays, and assays for HPP-CFCs), (2) granulocytes or neutrophils (clonal agar or methyl cellulose assays wherein the medium contains G-CSF or GM-CSF), (3) megakaryocytes (clonal agar or methyl cellulose assays wherein the medium contains TPO, IL-3, IL-6 and IL-11), and (4) erythroid cells (clonal agar or methyl cellulose assays wherein the medium contains EPO and SCF or EPO, SCF and IL-3).

It will be understood that the exact nature of such phenotypic and biological assays will vary dependent upon the condition being treated and whether the treatment is directed to enhancing the population of hematopoietic stem cells or the population of cells of a particular lineage or lineages.

In cases where the subject has been diagnosed as having a particular type of cancer, the status of the cancer is also monitored using diagnostic techniques appropriate to the type of cancer under treatment to determine if a slowing or diminution of the growth of cancer cells or a solid tumor has taken place, or a reduction in the total number of cancer cells or total tumor burden can be detected. Techniques routinely employed by practitioners in the field of cancer therapy include one or more of biopsy, ultrasound, X-ray, magnetic resonance imaging (MRI), analysis or bone marrow aspirates, etc.

The antisense oligomer treatment regimen may be adjusted (dose, frequency, route, etc.), as indicated, based on the results of the phenotypic and biological assays described above.

C. Compositions of the Invention

The antisense oligonucleotides of the invention and pharmaceutical compositions containing them are useful for inhibiting abnormal cell proliferation and retarding or arresting the growth of cancer cells.

The antisense oligonucleotides of the invention can be effective in the treatment of patients with certain cancers, for modulating the cell division and/or differentiation properties of cancer cells such that growth of the cancer cells is retarded or arrested, as evidenced by a slowing or diminution of a the growth of cancer cells or a solid tumor, or a reduction in the number of cancer cells or total tumor burden. In other words, the cancer cells are decreased in number or eliminated, with little or no detrimental effect on the normal growth or development of non-cancer cells surrounding such cancer cells.

Preferred antisense oligonucleotides for practicing the present invention block or inhibit translation of the mRNA containing the target sequence; and/or modify the processing of an mRNA to produce a splice variant of the mRNA.

Exemplary preferred antisense oligonucleotides according to the present invention include an antisense oligonucleotide complementary to a sequence spanning the AUG initiation codon of a sequence preferentially expressed in hematopoietic stem cells, but not more mature cells, exemplified by the following: (1) an antisense oligonucleotide complementary to a sequence spanning the AUG initiation codon of the human EVI-1 zinc finger gene, exemplified by the sequence presented as SEQ ID NO:1; (2) an antisense oligonucleotide complementary to a sequence spanning the AUG initiation codon of the human serum-deprivation response gene, exemplified by the sequence presented as SEQ ID NO:2; (3) an antisense oligonucleotide complementary to a sequence spanning the AUG initiation codon of the human multimerin gene, exemplified by the sequence presented as SEQ ID NO:3; (4) an antisense oligonucleotide complementary to a sequence spanning the AUG initiation codon of the human tissue transglutaminase gene, exemplified by the sequence presented as SEQ ID NO:4; (5) an antisense oligonucleotide complementary to a sequence spanning the AUG initiation codon of the human FE65 gene, exemplified by the sequence presented as SEQ ID NO:5; (6) an antisense oligonucleotide complementary to a sequence spanning the AUG initiation codon of the human RAB27 gene, exemplified by the sequence presented as SEQ ID NO:6; (7) an antisense oligonucleotide complementary to a sequence spanning the AUG initiation codon of the human Jagged2 gene, exemplified by the sequence presented as SEQ ID NO:7; an antisense oligonucleotide complementary to a sequence spanning the AUG initiation codon of the human Notch1 (Tan-1) gene; and an antisense oligonucleotide complementary to a sequence spanning the AUG initiation codon of the murine Notch1 gene, and the human Notch2 and Notch3 genes, exemplified by the sequences presented as SEQ ID NOs:12, 10 and 11, respectively.

VI. Utility

Stem cells, e.g. HSC, treated with one or more of the antisense oligonucleotides described herein find utility in a variety of applications. For example, they can be used to promote the differentiation of immature cells, e.g. hematopoietic stem cells associated with a particular disease state, such as cancer. In addition, they can be used as a source of cells for repopulating a subject with various hematopoietic cell lineages, by providing for their maturation and differentiation.

The antisense oligomers of the invention are effective to promote cellular maturation and differentiation. For example, ex vivo antisense oligomer-treated stem cells may serve be used to generate an expanded population of committed progenitor cells and their progeny. For example, the invention provides a means to produce more differentiated cells from a hematopoietic stem cell, such as monocytes, granulocytes, platelets, lymphocytes and red blood cells.

Treatment of HSC with one or more of the antisense oligonucleotides described herein further provides a means to release HSC from a resting (quiescent) or $G_o$ state into cell cycle, and hence a treatment for hematopoietic dysfunction related thereto.

Such ex vivo expanded cell populations find utility in both autologous and allogeneic hematopoietic engraftment when readministered to a patient.

Such methods may be used in the treatment of neoplastic disease and can be effective to result in a slowing or diminution of the growth of cancer cells or a solid tumor, or a reduction in the total number of cancer cells or total tumor burden in the patient under treatment and/or a more rapid recovery of a functional hematopoietic system following radiation or chemotherapy, e.g., more rapid recovery of neutrophil and platelet cell populations.

Exemplary therapeutic regimens for treatment of cancer patients include ex vivo treatment of hematopoietic stem cells with the antisense oligonucleotides described herein, together with chemotherapy, radiation therapy, or other treatment methods known in the art to treat the subject cancer.

The following examples illustrate but are not intended in any way to limit the invention.

EXAMPLE 1
Identification of Differentiation-Associated mRNAs cDNA libraries were made from LTR-hematopoietic stem cells and slightly differentiated cells (STR-HSC) from quiescent animals and the mRNA expression profiles compared. Genes preferentially expressed in LTR-hematopoietic stem cells were detected using gene expression fingerprinting (GEF) and representational differential analysis (RDA).

The mRNA expression pattern was compared for unfractionated bone marrow (unf BM), the population of cells selected by depletion of lineage-committed cells using Dynal Beads coupled with lineage specific monoclonal antibodies, and hematopoietic stem cells characterized as short term repopulating HSCs (STR-HSC), or long term repopulating HSCs (LTR-HSC), using GEF and RDA.

Seven mRNAs preferentially expressed in LTR-HSCs were identified and further characterized including: the EVI-1 zinc finger gene, the serum-deprivation response gene, the multimerin gene, the tissue transglutaminase gene, the FE6S gene, the RAB27 gene and the Jagged2 gene, as presented in table 1.

TABLE 1

Genes preferentially expressed in LTR-HSC.

| Genes preferentially expressed in LTR-HSC | Unf BM | | Lin- | | STR-HSC | LTR-HSC Lin-, c- |
|---|---|---|---|---|---|---|
| | c-kit- | c-kit+ | c-kit- | c-kit+ | Lin-, c-kit+ $Ho^{low}$, $Rh^{high}$ | kit+ $Ho^{low}$, $Rh^{high}$ |
| Evi-1 zinc finger protein | − | − | − | − | − | + |
| Serum deprivation response (SDR) gene | − | − | − | − | − | + |
| Multimerin | − | − | − | − | +/− | + |
| Tissue Trans-glutaminase | − | − | − | +/− | +/− | ++ |
| Fe65 mRNA | − | − | − | ++ | +/− | ++ |
| RAB27 | − | − | − | + | +/− | + |
| Jagged2 | − | + | − | + | ++ | ++ |

EXAMPLE 2
Hematotoietic Stem Cell Isolation and Treatment with Antisense Oligonucleotides.

Murine hematopoietic stem cells were obtained from bone marrow starting with unfractionated bone marrow, performing a density separation using 1.080 g/ml Nycodenz separation medium (Nycomed Pharma AS OSLO, Norway), followed by isolation of the lin− cell population using Dynal Bead depletion employing lineage-specific monoclonal antibodies, followed by staining with: (I) antibodies to c-kit and Sca 1; (2) propidium iodide (PI); and (3) the dyes, Hoescht 33342, Rhodamine 123. The cells were subjected to FACS and two populations selected for based on phenotypic markers: (A) Sca 1+, c-kit+, lin−, Hoescht 33342 low ($Ho^{low}$), Rhodamine 123 low ($Rh^{low}$) and PI negative cells (LTR-HSC), or (B) Sca 1+, c-kit+, lin− cells, (STR-HSC).

25 cells enriched for LTR-HSC, characterized as described above were sorted directly into medium containing interleukin-6 (IL-6) and stem cell factor (SCF), with or without antisense oligomers and assayed after 5 days for HPP-CFC formation.

TABLE 2

EVI-1 antisense-induced differentiation of LTR-HSC in vitro

| Conditions | Total number of clonogenic cells at day 5 | Total number of HPP-CFC at day 5 | % of HPP-CFC (HPP-CFC/ clonogenic cells) |
|---|---|---|---|
| IL-6 + SCF control | 201 ± 32 | 88 ± 14 | 44 ± 7 |
| scrambled c-myc AS control 25 µM | 129 ± 34 | 80 ± 15 | 63 ± 4 |
| IL-6 + SCF + 125 µM AS to EVI-1 | 186 ± 36 | 45 ± 12 | 25 ± 10 |
| IL-6 + SCF + 25 µM AS to EVI-1 | 228 ± 58 | 46 ± 15 | 18 ± 9 |
| IL-6 + SCF + 5 µM AS to EVI-1 | 140 ± 2 | 34 ± 8 | 24 ± 5 |
| IL-6 + SCF + 1 µM AS to EVI-1 | 133 ± 11 | 53 ± 16 | 40 ± 10 |

Figure 1A:
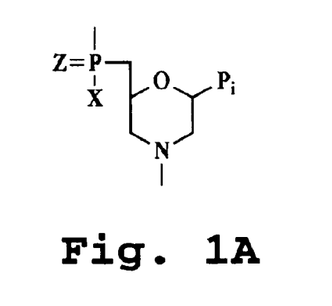
FIG. 1A-E show several preferred morpholino subunits having 5-atom (A), six-atom (B) and seven-atom (C–E) linking groups suitable for forming polymers.
Figure 1B:
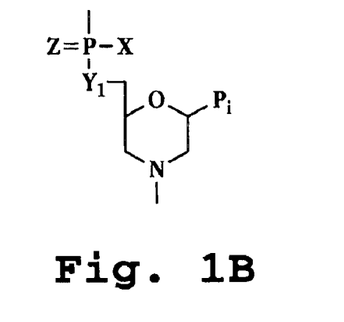
Figure 1C:
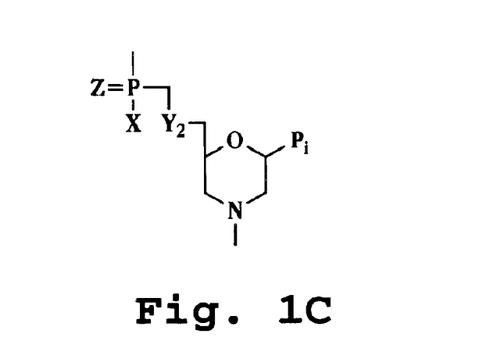
Figure 1D:
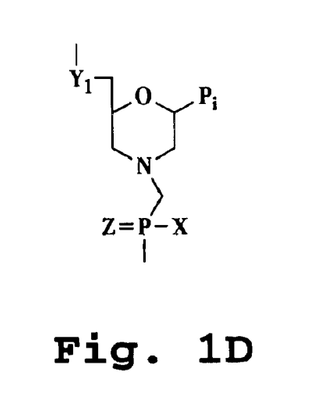
Figure 1E:
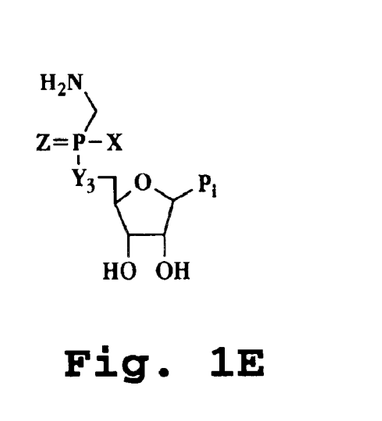
Figure 2A:
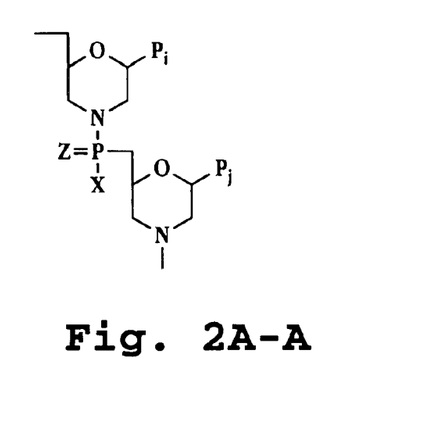
Figure 2B:
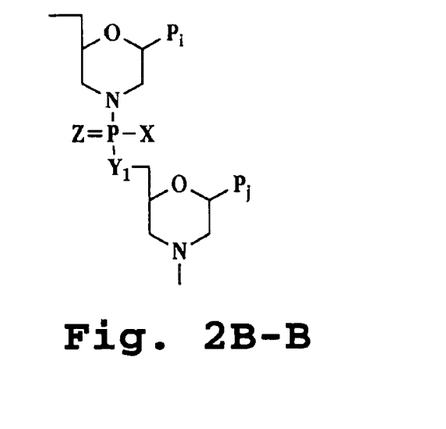
Figure 2C:
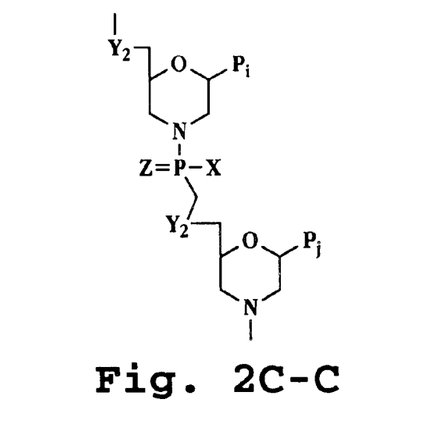
Figure 2D:
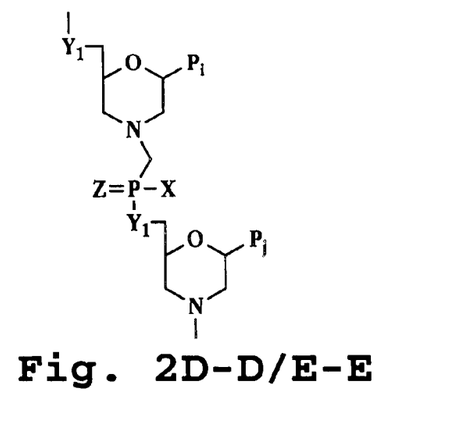
Figure 3:
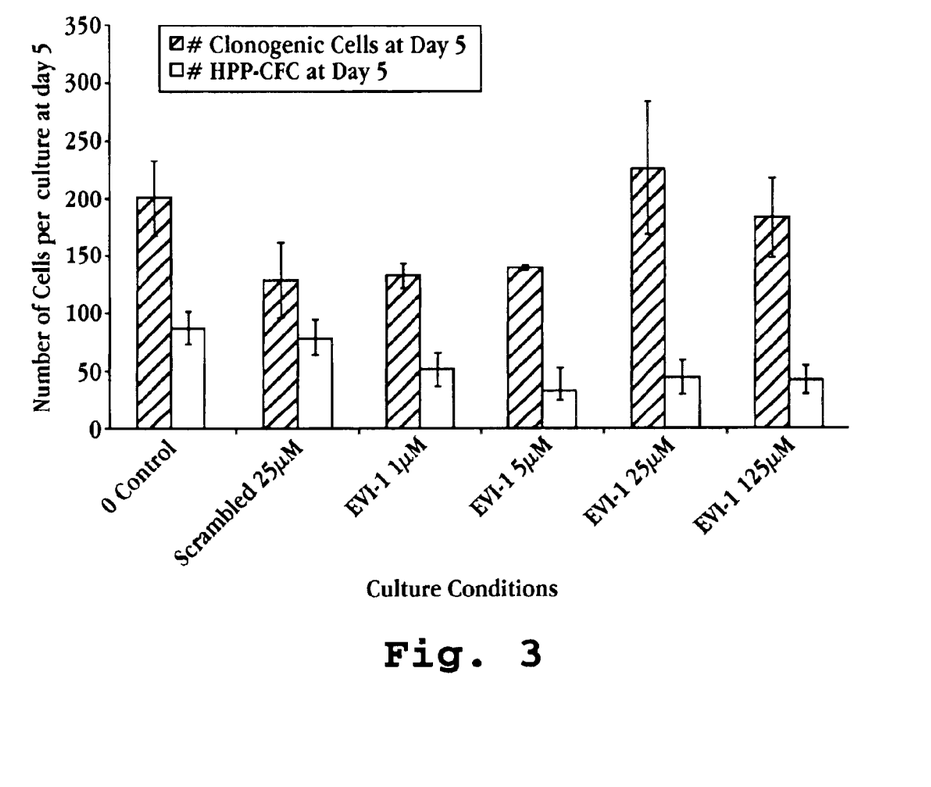
FIG. 3 depicts the results of an in vitro assay for HSC differentiation, wherein the effect of various concentrations of antisense oligonucleotides on the number of clonogenic cells (solid bars) and HPP-CFCs (patterned bars), at day 5 is presented, wherein clonogenic cells are defined as cells that proliferate and form clones under a given set of culture conditions.

The assay results indicate that exposure of cells to antisense to EVI-1 yields a decrease in HPP-CFC at concentrations as low as 1 µM, indicating differentiation or maturation of hematopoietic stem cells, as detailed in Table 2 and FIG. 3 (with results reported as the mean±SEM).

The results presented herein show the utility of antisense oligomers complementary to a sequence preferentially expressed in stem cells in promoting the differentiation of hematopoietic stem cells from the characteristic hematopoietic stem cell phenotype.

| Description | SEQ ID NO |
|---|---|
| antisense to EVI-1 zinc finger gene 5'-GCT CTT CAT GAA CAG CAG AAG-3' | 1 |
| antisense to serum-deprivation response gene 5'-CCT CTC CCA TGG CTG GGC AG-3' | 2 |
| antisense to prepromultimerin gene 5'-CCC TTC ATC TCA GTA GTT TG-3' | 3 |
| antisense to tissue transglutaminase gene 5'-CCT CGG CCA TGG TCG GGC GG-3' | 4 |
| antisense to FE65 5'-GGA ACA GAC ATG GCC TTG GC-3' | 5 |
| antisense to RAB27 5'-CTC CAT CAG ACA TAA TGA AG-3' | 6 |
| antisense to human Jagged2 5'-CGC CCG CAT TGC CCC CGC GA-3' | 7 |
| antisense to c-myc AVI 4126 5'-ACG TTG AGG GGC ATC GTC GC-3' | 8 |
| antisense to human Notch1 5'-GGC GCC AGG AGC GGC GGC AT-3' | 9 |
| antisense to human Notch2 5'-GCA CTC ATC CAC TTC ATA CTC-3' | 10 |
| antisense to human Notch3 5'-GAC TTG GCT TCT CCC TCC TA-3' | 11 |
| antisense to murine Notch1 5'-ACG GAT GTC CAT GGG GTC CA-3' | 12 |

What is claimed:

1. A method of promoting hematopoietic stem cell differentiation in vitro, the method comprising:

contacting hematopoietic stem cells in vitro with an antisense morpholino oligomer having a substantially uncharged backbone, which oligomer comprises SEQ ID NO:1, and has a maximum length of 40 nucleotides, wherein said contacting results in a decrease in the number of high proliferative potential colony forming cells (HPP-CFC) relative to the number of clonogenic cells, as compared to stem cells not contacted with said oligomer and which decrease in HPP-CFC is indicative of hematopoietic stem cell differentiation.

2. The method of claim 1, wherein said antisense morpholino oligomer comprises phosphorodiamidate intersubunit linkages, joining a morpholino nitrogen of one morpholino subunit to a 5-exocyclic carbon of an adjacent morpholino subunit.

3. The method of claim 1, wherein said hematopoietic stem cells are provided by:

(a) obtaining a stem cell-containing cell population from a subject; and (b) treating the cell population in manner effective to enrich the cell population for stem cells.

4. A composition comprising an antisense oligomer having an uncharged backbone, wherein said antisense oligomer is characterized by (a) the ability to hybridize with the complementary sequence of a target RNA with high affinity at a Tm greater than 50° C., (b) nuclease resistance, and (c) the capability for active or facilitated transport into cells; and has the sequence presented as SEQ ID NO:1, and has a maximum length of 40 nucleotides.

5. An antisense morpholino oligomer characterized by a backbone which is substantially uncharged, wherein said oligomer has the base sequence presented as SEQ ID NO:1 and has a maximum length of 40 nucleotides.

* * * * *

SEQUENCE LISTING

<160> NUMBER OF SEQ ID NOS: 12

<210> SEQ ID NO 1
<211> LENGTH: 21
<212> TYPE: DNA
<213> ORGANISM: Artificial Sequence
<220> FEATURE:
<223> OTHER INFORMATION: antisense

<400> SEQUENCE: 1
gctcttcatg aacagcagaa g                                              21

<210> SEQ ID NO 2
<211> LENGTH: 20
<212> TYPE: DNA
<213> ORGANISM: Artificial Sequence
<220> FEATURE:
<223> OTHER INFORMATION: antisense

<400> SEQUENCE: 2
cctctcccat ggctgggcag                                                20

<210> SEQ ID NO 3
<211> LENGTH: 20
<212> TYPE: DNA
<213> ORGANISM: Artificial Sequence
<220> FEATURE:
<223> OTHER INFORMATION: antisense

<400> SEQUENCE: 3
cccttcatct cagtagtttg                                                20

<210> SEQ ID NO 4
<211> LENGTH: 20
<212> TYPE: DNA
<213> ORGANISM: Artificial Sequence
<220> FEATURE:
<223> OTHER INFORMATION: antisense

<400> SEQUENCE: 4
cctcggccat ggtcgggcgg                                                20

<210> SEQ ID NO 5
<211> LENGTH: 20
<212> TYPE: DNA
<213> ORGANISM: Artificial Sequence
<220> FEATURE:
<223> OTHER INFORMATION: antisense

<400> SEQUENCE: 5
ggaacagaca tggccttggc                                                20

<210> SEQ ID NO 6
<211> LENGTH: 20
<212> TYPE: DNA
<213> ORGANISM: Artificial Sequence
<220> FEATURE:
<223> OTHER INFORMATION: antisense

<400> SEQUENCE: 6
ctccatcaga cataatgaag                                                20

<210> SEQ ID NO 7
<211> LENGTH: 20

```
<212> TYPE: DNA
<213> ORGANISM: Artificial Sequence
<220> FEATURE:
<223> OTHER INFORMATION: antisense

<400> SEQUENCE: 7
cgcccgcatt gcccccgcga                                               20

<210> SEQ ID NO 8
<211> LENGTH: 20
<212> TYPE: DNA
<213> ORGANISM: Artificial Sequence
<220> FEATURE:
<223> OTHER INFORMATION: antisense

<400> SEQUENCE: 8
acgttgaggg gcatcgtcgc                                               20

<210> SEQ ID NO 9
<211> LENGTH: 20
<212> TYPE: DNA
<213> ORGANISM: Artificial Sequence
<220> FEATURE:
<223> OTHER INFORMATION: antisense

<400> SEQUENCE: 9
ggcgccagga gcggcggcat                                               20

<210> SEQ ID NO 10
<211> LENGTH: 21
<212> TYPE: DNA
<213> ORGANISM: Artificial Sequence
<220> FEATURE:
<223> OTHER INFORMATION: antisense

<400> SEQUENCE: 10
gcactcatcc acttcatact c                                             21

<210> SEQ ID NO 11
<211> LENGTH: 20
<212> TYPE: DNA
<213> ORGANISM: Artificial Sequence
<220> FEATURE:
<223> OTHER INFORMATION: antisense

<400> SEQUENCE: 11
gacttggctt ctccctccta                                               20

<210> SEQ ID NO 12
<211> LENGTH: 20
<212> TYPE: DNA
<213> ORGANISM: Artificial Sequence
<220> FEATURE:
<223> OTHER INFORMATION: antisense

<400> SEQUENCE: 12
acggatgtcc atggggtcca                                               20
```